(12) United States Patent
Fujinami

(10) Patent No.: US 6,509,299 B2
(45) Date of Patent: Jan. 21, 2003

(54) PYRONE COMPOUNDS AND THERE USE

(75) Inventor: Michihiko Fujinami, Minoo (JP)

(73) Assignee: Sumitomo Chemical Company, Limited, Josaka (JP)

( * ) Notice: Subject to any disclaimer, the term of this patent is extended or adjusted under 35 U.S.C. 154(b) by 0 days.

(21) Appl. No.: 10/136,271

(22) Filed: May 2, 2002

(65) Prior Publication Data

US 2002/0197294 A1 Dec. 26, 2002

(30) Foreign Application Priority Data

Jun. 8, 2001 (JP) ........................................ 2001-173728

(51) Int. Cl.⁷ ............................................... A01N 43/02
(52) U.S. Cl. ........................................ 504/292; 549/291
(58) Field of Search ........................... 549/291; 504/292

(56) References Cited

U.S. PATENT DOCUMENTS

| 3,336,339 A | 8/1967 | England |
| 3,825,599 A | 7/1974 | England |
| 6,215,016 B1 | 4/2001 | Kawai et al. |

FOREIGN PATENT DOCUMENTS

| DE | 238048 A1 | 8/1986 |
| GB | 1258033 | 5/1969 |
| JP | 51-19126 A | 2/1976 |

OTHER PUBLICATIONS

Y. Qamar et al., Synthesis of 2–Aryl–7–methylpyrano[4,3–b]–pyran–4 (*H*)–diones, Indian Journal of Chemistry, vol. 27B, (1988), pp. 373.

T. Harris et al., "Bromination of Dehydroacetic Acid", J. Org. Chem., vol. 35, No. 5, (May 1970), pp. 1329–1333.

D.C. England, "Synthesis and Chemistry of a Perfluoroacylketones and a Related Perfluorovinyl Ketones", J. Org. Chem. vol. 46, (1981), pp. 147–153.

*Primary Examiner*—Amelia Owens
(74) *Attorney, Agent, or Firm*—Sughrue Mion, PLLC

(57) ABSTRACT

A pyrone compound given by formula (1)

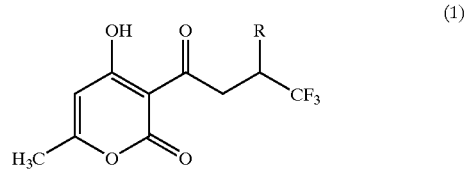

wherein R represents a trifluoromethyl group, hydrogen atom or methyl group, has an excellent effect for controlling harmful pests.

9 Claims, No Drawings

PYRONE COMPOUNDS AND THERE USE

FIELD OF THE INVENTION

The present invention relates to pyrone compounds and their pesticidal use.

BACKGROUND ART

JP51-19126A discloses that some pyrone compounds have insecticidal/acaricidal activity. However, their compounds are not satisfactorily effective for controlling harmful pests.

SUMMARY OF THE INVENTION

The present invention provides a compound given by formula

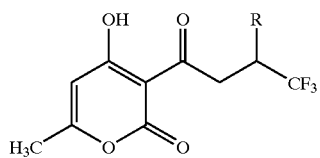

(1)

wherein R represents a trifluoromethyl group, hydrogen atom or methyl group, a pesticidal composition comprising it as an active ingredient and a method for controlling pests comprising applying it to pests or a place where pests inhabit.

The present compound has an excellent pesticidal activity.

DISCLOSURE OF THE INVENTION

A process for producing the present compound is explained below.

The present compound can be produced by the method given by the scheme below, namely reaction of 4-hydroxy-6-methyl-2-pyrone given by formula (2) with a carboxylic acid given by formula (3):

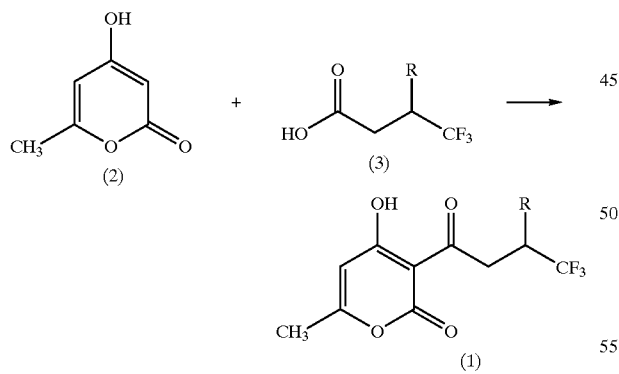

wherein R has the same meaning above.

The reaction is usually carried out in a solvent in the presence of a condensing agent (e.g. dicyclohexylcarbodiimide) and 4-dimethylaminopyridine.

Examples of the solvent to be used for the reaction include aliphatic hydrocarbons such as hexane, heptane, octane and nonane; aromatic hydrocarbons such as toluene, xylene and mesitylene; halogenated hydrocarbons such as chlorobenzene, dichlorobenzene and benzotrifluoride; ethers such as diisopropyl ether, 1,4-dioxane, tetrahydrofuran, ethylene glycol dimethyl ether and diethylene glycol dimethyl ether; acid amides such as N,N-dimethylformamide and N,N-dimethylacetamide; sulfur-containing solvents such as dimethyl sulfoxide and sulfolane; and mixtures thereof.

In the reaction, the amount ratio of the compound given by formula (3) is 0.7 to 1.5 moles based on 1 mole of the compound given by formula (2).

The amount ratio of the reagents is 1 to 5 moles of the condensing agent and 0.01 to 1 mole of 4-dimethylaminopyridine based on 1 mole of the compound given by formula (2).

The reaction temperature is usually within a range from 0° C. to 100° C., and the reaction time is usually within a range from 1 to 48 hours though it depends on the reaction temperature.

After the completion of the reaction, the reaction mixture can be, for example, subjected to a filtration, washing the filtrate with an acidic water, drying and then concentration, optionally purification such as chromatography, to give the present compound as an isolated product.

Examples of the pests against which the present compound exhibits a control effect include the following arthropods: Hemipteran pests: Delphacidae (planthoppers) [e.g. *Laodelphax striatellus* (small brown planthopper), *Nilaparvata lugens* (brown planthopper) and *Sogatella furcifera* (white-backed rice planthopper)], Deltocephalidae (leafhoppers) [e.g. *Nephotettix cincticeps, Nephotettix virescens* and *Recilia dorsalis*], Aphididae (aphids), stinkbugs, Aleyrodidae (whiteflies), scales, Tingidae (lace bugs) and Psyllidae (suckers);

Lepidopteran pests: Pyralidae [e.g. *Chilo suppressalis* (rice stem borer), *Cnaphalocrocis medinalis* (rice leafroller) and *Plodia interpunctella* (Indian meal moth)], Noctuidae [e.g. *Spodoptera litura* (tobacco cutworm), *Pseudaletia separata* (rice armyworm), *Mamestra brassicae* (cabbage armyworm), Plusiinae, *Agrotis* spp. containing *Agrotis segetum* (turnip cutworm) and *Agrotis ipsilon* (black cutworm), Helicoverpa spp. and Heliothis spp.], Pieridae [e.g. *Pieris rapae*], Tortricidae [e.g. Adoxophyes spp.], Carposinidae, Lyonetiidae, Lymantriidae, Yponameutidae [e.g. *Plutella xylostella*], Hesperiidae [e.g. *Parnara guttata*], Tineidae [e.g. *Tinea translucens* (casemaking clothes moth) and *Tineola bisselliella* (webbing clothes moth)];

Dipteran pests: Culex spp. [e.g. *Culex pipiens pallens* and *Culex tritaeniorhynchus*], Aedes spp. [e.g. *Aedes aegypti* (yellow fever mosquito) and *Aedes albopictus*], Anopheles spp. [e.g. *Anopheles sinensis*], Chironomidae (midges), Muscidae [e.g. *Musca domestica* (housefly), *Muscina stabulans* (false housefly) and *Fannia canicularis* (little house fly)], Calliphoridae, Sarcophagidae, Anthomyiidae [e.g. *Delia platura* (seedcorn maggot) and *Delia antiqua* (onion maggot)], Tephritidae (fruit flies), Drosophilidae (vinegar flies), Psychodidae (sand flies), Tabanidae, Simuliidae (black flies), Stomoxyidae (stable flies), Phoridae and Ceratopogonidae (biting midges);

Coleopteran pests: corn rootworms [e.g. *Diabrotica virgifera virgifera* (western corn rootworm) and *Diabrotica undecimpunctata howardi* (southern corn rootworm)], Scarabaeidae [e.g. *Anomala cuprea* and *Anomala rufocuprea*], Curculionidae (weevils) [e.g. *Sitophilus zeamais* (maize weevil) and *Lissorhoptrus oryzophilus* (ricewater weevil), Dermestidae [e.g. *Authrenus verbasci* and *Attagenus unicolor japonicus*], Tenebrionidae (darkling beetles) [e.g. *Tenebrio molitor*

(yellow mealworm) and *Tribolium castaneum* (red flour beetle)], Chrysomelidae (leaf beetles) [e.g. *Oulema oryzae* (rice leaf beetle), *Phyllotreta striolata* (striped flea beetle) and *Aulacophora femoralis* (cucurbit leaf beetle), Anobiidae, Coccinellidae (ladybirds). [e.g. *Epilachna vigintioctopunctata*], Lyctidae (powderpost beetles), Bostrychidae, Cerambycidae and Staphylinidae [e.g. *Paederus fuscipes*];

Dictyopteran pests: *Blattella gezmanica* (German cockroach), *Periplaneta fuliginosa* (smokybrown cockroach), *Periplaneta americana* (American cockroach), *Periplaneta brunnea* (brown cockroach) and *Blatta orientalis* and so on;

Thysanopteran pests: Thripidae [e.g. *Thrips palmi*, *Frankliniella occidentalis* (western flower thrips) and *Thrips hawaiiensis* (flower thrips)];

Hymenopteranpests: Formicidae (ants), Vespidae [e.g. hornets and long-legged wasps], Bethylidae and Tenthredinidae (sawflies) [e.g. *Athalia japonica* (cabbage sawfly)];

Orthopteran pests: Gryllotalpidae (mole crickets) and Acrididae (grasshoppers);

Siphonapteran pests: *Ctenocephalides canis* (dog flea), *Ctenocephalides felis* (cat flea) and *Pulex irritans* (human flea);

Anopluran pests: *humanus corporis*, *Pediculus capitis* and *Phthirus pubis* (crab louse);

Isopteran pests; *Reticulitezmes speratus* and *Coptotezmes fozmosanus;*

Acarina pests: Tetranychidae (spider mites) [e.g. *Tetranychus cinnabarinus* (carmine spider mite), *Tetranychus urticae* (two-spotted spider mite), *Tetranychus kanzawai* (Kanzawa spider mite), *Panonychus citri* (citrus red mite) and *Panonychus ulmi* (European red mite)], Ixodidae [e.g. *Boophilus microplus* and *Haemaphysalis longiconis*], Acaridae [e.g. *Tyrophagus putrescentiae* (copra mite) and *Aleuroglyphus ovatus*], Dermanyssidae [e.g. *Dermatophagoides farinae* (American house dust mite) and *Dermatophagoides ptrenyssnus*], Glycyphagidae [e.g. *Glycyphagus privates*, *Glycyphagus domesticus* and *Glycyphagus destructor*], Cheyletidae [e.g. *Cheyletus malaccensi* and *Cheyletus fortis*], Tarsonemidae, Chortoglyphus spp. and Haplochthonius spp.;

Isopoda pests: wood louse [e.g. *Porcellio scaber* and *Porcellionides pruinosus*] and pill-bugs [e.g. *Armadillidium vulgare*].

The pesticidal composition of the present invention comprises the present compound and an inert carrier, such as solid carrier, liquid carrier, gaseous carrier and/or bait material (poison bait material). The present compound may be impregnated with a base material (e.g. porous ceramic board, non-woven cloth, paper, mosquito-coil base). Further, the pesticidal composition of the present invention optionally comprises a surfactant or the other auxiliary to be formulated to oil solutions, emulsifiable concentrates, wettable powders, flowable formulations, granules, dusts, aerosols, foggings, heating fumigants, smokings, poison baits, microcapsule formulations, ULV formulations, spot-on formulations, pour-on formulations, shampoo formulations, sheet formulations, resin formulations and so on.

These formulations usually include the present compound as an active ingredient in an amount of 0.01 to 95% by weight.

Examples of the solid carrier to be used for the formulation include fine powder or granules of clays (e.g. kaolin clay, diatomaceous earth, synthetic hydrated silicon oxide, bentonite, Fubasami clay, acid clay), talc, ceramics, fertilizer (e.g. ammonium sulfate, ammonium phosphate, ammonium nitrate, ammonium chloride, urea) and other inorganic minerals (e.g. sericite, quartz, sulfur, activated carbon, calcium carbonate, hydrated silicon oxide).

Examples of the liquid carrier include water, alcohols (e.g. methanol, ethanol), ketones (e.g. acetone, methyl ethyl ketone), aromatic hydrocarbons (e.g. toluene, xylene, ethylbenzene, methylnaphthalene), aliphatic hydrocarbons (e.g. hexane, cyclohexane, kerosene, gas oil), esters (ethyl acetate, butyl acetate), nitriles (e.g. acetonitrile, isobutyronitrile), ethers (e.g. diisopropyl ether, dioxane), acid amides (e.g. N,N-dimethylformamide, N,N-dimethylacetamide), halogenated hydrocarbons (dichloromethane, trichloroethane, carbon tetrachloride), organic sulfur compounds (e.g. dimethyl sulfoxide) and vegetable oils (e.g. soybean oil, cottonseed oil).

Examples of the gaseous carrier include fluorocarbons, butanegas, LPG (liquefied petroleum gas), dimethyl ether and carbon dioxide.

Examples of the surfactant include alkyl sulfates, alkylsulfonates, alkylarylsulfonates, alkyl aryl ethers, polyoxyethylenealkyl aryl ethers, polyethylene glycol ethers, polyhydric alcohol esters and sugar alcohol derivatives.

Examples of the other auxiliaries include sticking agents, dispersing agent and stabilizing agents, typically, casein, gelatin, polysaccharides (e.g. starch, gum arabic, cellulose derivatives, alginic acid), lignin derivatives, synthetic water-soluble polymers (e.g. polyvinyl alcohol, polyvinylpyrrolidone, polyacrylic acids), PAP (acid isopropyl phosphate), BHT (2,6-di-tert-butyl-4-methyphenol), BHA (mixture of 2-tert-butyl-4-methoxyphenol and 3-tert-butyl-4-methoxyphenol), vegetable oils, mineral oils, fatty acids and esters of fatty acid.

The base material of the poison baits includes a bait component (e.g. grain powder, vegetable oil, sugar, cellulose), an antioxidant (e.g. dibutylhydroxytoluene, nordihydroguaiaretic acid), a preservative (e.g. dehydroacetic acid), a substance for preventing erroneous eating from children and pets (e.g. red pepper powder), a pest-attractant flavor (e.g. cheese flavor, onion flavor, peanut oil).

When the present pesticidal composition is applied for controlling agricultural or forestry pests, the application dosage of the present compound is usually 1 to 10 000 g per 1 hectare. Emulsifiable concentrates, wettable powders and flowable formulations are diluted with water to the concentration of 10 to 10000 ppm and applied. Granules and dusts are usually used as prepared. These formulations can be applied directly to the pests or to plants which are crops to be protected from the pests. Further, they may be applied to soil for controlling the pests living in the soil.

When the present pesticidal composition is applied for hygienic use, emulsifiable concentrates, wettable powders and flowable formulations are diluted with water to the concentration of 0.01 to 10000 ppm and applied to pests or a place the pests inhabit. Oil solutions, aerosols, smokings and poison baits are applied to pests or a place the pests inhabit as prepared. Fumigants are applied by heating to volatile the active ingredient at a place the pests inhabit. The application dosage of the present compound is usually 0.001 to 5 g/m$^2$ of the floor or 0.01 to 10 g/m$^3$ of the space.

The present pesticidal composition can be used together with the other insecticide, acaricide, nematocide, fungicide, herbicide, plant growth regulator, synergist, fertilizer, soil-improving agent, animal food and so on.

Examples of the insecticides, acaricides and nematocides include organophosphorus compounds such as fenitrothion, fenthion, diazinon, chlorpyrifos, acephate, methidathion, disulfoton, DDVP, sulprofos, cyanophos, dioxabenzofos, dimethoate, phenthoate, malathion, trichlorfon, azinphosmethyl, monocrotophos and ethion; carbamate compounds such as BPMC, benfracarb, propoxur, carbosulfan, carbaryl, methomyl, ethiofencarb, aldicarb, oxamyl and fenothiocarb; pyrethroid compounds such as etofenprox, fenvalerate, esfenvalerate, fenpropathrin, cypermethrin, permethrin, cyhalothrin, deltamethrin, cycloprothrin, fluvalinate, bifenthrin, tralomethrin, silafluofen, d-phenothrin, d-allethrin, cyphenothrin, d-resmethrin, acrinathrin, cyfluthrin, tefluthrin, transfluthrin, tetramethrin, allethrin, prallethrin, empenthrin, imiprothrin and d-furamethrin; thiadiazine derivatives such as buprofezin; nitroimidazolidine derivatives; nereistoxin derivatives such as cartap, thiocyclam and bensultap; neonicotinoid compounds such as acetamiprid, thiamethoxam and thiacloprid; chlorinated hydrocarbons such as endosulfan, γ-BHC and DDT; benzoylphenylurea compounds such as chlorfluazuron, teflubenzuron and flufenoxuron; formamidine derivatives such as amitraz and chlordimeform; thiourea derivatives such as diafenthiuron; phenylpyrazole compounds; metoxadiazone; bromopropylate; tetradifon; chinomethionat; propargite; fenbutatin oxide; hexythiazox; clofentezine; pyridaben; fenpyroximate; tebufenpyrad; polynactins complex [tetranactin, dinactin and trinactin]; pyrimidifen; milbemectin; abamectin; ivermectin and azadirachtin [AZAD].

EXAMPLES

The present invention will be further illustrated in detail by the production examples, formulation examples and test examples, although the present invention is not limited in any sense to these examples.

The production examples are shown as follows.

Production Example 1

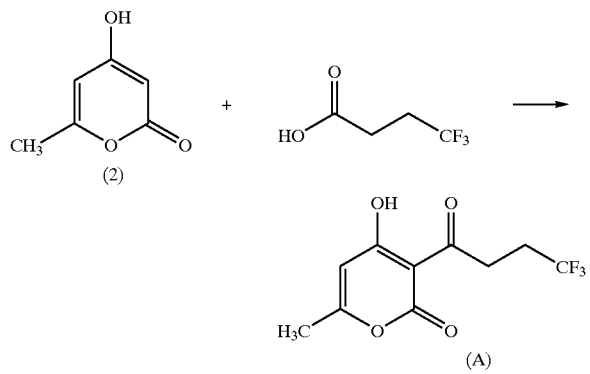

In 240 ml of toluene, 14.1 g of 4-hydroxy-6-methyl-2-pyrone was suspended, and 1.94 g of 4-dimethylaminopyridine, 16.6 g of 4, 4,4-trifluorobutyric acid and 21.9 g of dicyclohexylcarbodiimide were added thereto. The reaction mixture was stirred for 1 hour at room temperature and further stirred for 20 hours at 70° C. After cooling to room temperature, it was subjected to filtration. The filtrate was washed with 1% hydrochloric acid twice and saturated brine once in this order. The organic layer was dried over anhydrous sodium sulfate and concentrated under reduced pressure. The residue was subjected to silica gel chromatography to give 5.38 g of 4-hydroxy-6-methyl-3-(4, 4,4-trifluorobutyryl)-2-pyrone (hereinafter, referred to as the present compound (A)) mp 104° C.

$^1$H-NMR (250 MHz, CDCl$_3$/TMS): δ(ppm) 16.01(s,1H), 5.98(s,1H), 3.38(t,J=7.5 Hz,2H), 2.62–2.42(m,2H), 2.30(s, 3H)

Production Example 2

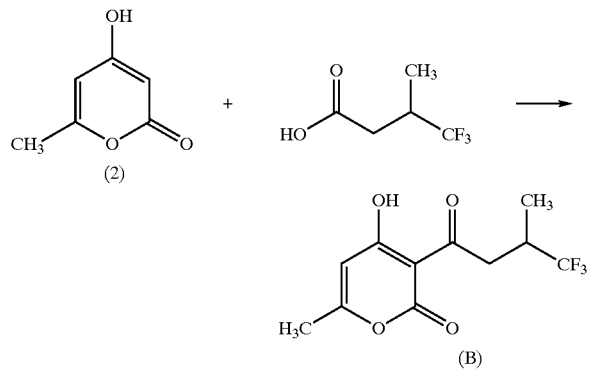

By the same manner as Production example 1, 0.46 g of 4-hydroxy-6-methyl-3-(3-trifluoromethylbutyryl)-2-pyrone (hereinafter, referred to as the present compound (B)) was obtained from 2.00 g of 4-hydroxy-6-methyl-2-pyrone, 240 mg of 4-dimethylaminopyridine, 2.48 g of 3-methyl-4,4,4-trifluorobutyric acid, 3.27 g of dicyclohexylcarbodiimide and 100 ml of toluene. mp 69° C.

$^1$H-NMR (250 MHz, CDCl$_3$/TMS): δ(ppm) 16.17(s,1H), 5.97(s,1H), 3.41(dd,J=18.3,4.1 Hz,1H), 3.18(dd,J=18.3,8.6 Hz,1H), 3.10–2.90 (m,1H), 2.29(s,3H), 1.18(d,J=6.8 Hz,3H)

Production Example 3

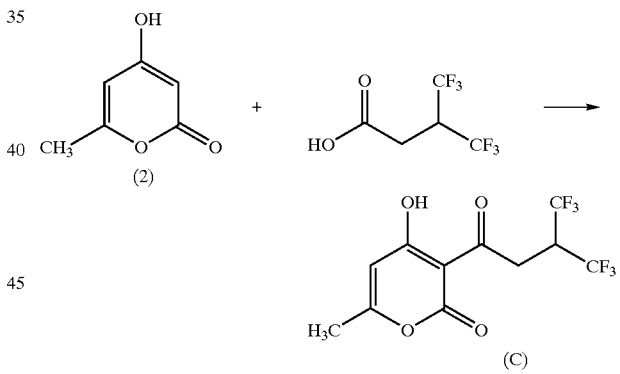

By the same manner as Production example 1, 0.17 g of 4-hydroxy-6-methyl-3-(3-trifluoromethyl-4,4,4-trifluorobutyryl) -2-pyrone (hereinafter, referred to as the present compound (C)) was obtained from 1.58 g of 4-hydroxy-6-methyl-2-pyrone, 220 mg of 4-dimethylaminopyridine, 2.50 g of 3-trifluoromethyl-4,4, 4-trifluorobutyric acid, 2.60 g of dicyclohexylcarbodiimide and 70 ml of toluene. mp 73° C.

$^1$H-NMR (300 MHz, CDCl$_3$/TMS): δ(ppm) 15.48(s,1H), 6.01(s,1H), 4.15–4.00(m,1H), 3.60(d,J=5.3 Hz,2H), 2.32(s, 3H)

Next, formulation examples are described below. Parts represent parts by weight.

Formulation Example 1

Ten parts of the present compound (A), (B) or (C), 17.5 parts of ammonium polyoxyethylenealkyl ether sulfate and 17.5 parts of silica are mixed with 55 parts of water under wet pulverizing to give each of formulations.

Formulation Example 2

Fifty parts of the present compound (A), (B) or (C), 3 parts of calcium ligninsulfonate, 2 parts of sodium laurylsulfate and 45 parts of synthetic hydrated silicon oxide are well pulverized and mixed to give each of wettable powders.

Formulation Example 3

Two parts of the present compound (A), (B) or (C), 88 parts of kaolin clay and 10 parts of talc are well pulverized and mixed to give each of dusts.

Formulation Example 4

Twenty parts of the present compound (A), (B) or (C), 14 parts of polyoxyethylenestyryl phenyl ether, 6 parts of calcium dodecylbenzenesulfonate and 60 parts of xylene are well mixed to give each of emulsifiable concentrates.

Formulation Example 5

Two parts of the present compound (A), (B) or (C), 1 part of synthetic hydrated silicon oxide, 2 parts of calcium ligninsulfonate, 30 parts of bentonite and 65 parts of kaolin clay are well pulverized and mixed, kneaded with water, and then granulated and dried to give each of granules.

Formulation Example 6

Twenty parts of the present compound (A), (B) or (C), 1.5 parts of sorbitan trioleate and 28.5 parts of aqueous solution containing 2 parts of polyvinyl alcohol are mixed and pulverized with a sand-grinder to make the particle diameter 3 μm or less. Forty parts of aqueous solution containing 0.05 part of xanthan gum and 0.1 part of aluminum magnesium silicate are added thereto and further mixed with 10 parts of propylene glycol to each of 20% flowable formulations.

Formulation Example 7

One-tenth (0.1) part of the present compound (A), (B) or (C) is dissolved in 5 parts of xylene and 5 parts of trichloroethane, and then mixed with 89.9 parts of deodorized kerosene to give each of 0.1% oil solution.

Formulation Example 8

An aerosol vessel is filled with the solution obtained by dissolving 0.1 part of the present compound (A), (B) or (C), 0.2 part of tetramethrin and 0.1 part of d-phenothrin with 10 parts of trichloroethane and 59.6 parts of deodorized kerosene. The vessel is then equipped with a valve and 30 parts of propellant (liquefied petroleum gas) is charged through the valve into the aerosol vessel under pressure to give each of oil-based aerosols.

Formulation Example 9

An aerosol vessel is filled with 50 parts of purified water and a mixture of 0.2 part of the present compound (A), (B) or (C), 0.2 part of d-allethrin, 0.2 part of d-phenothrin, 5 parts of xylene, 3.4 parts of deodorized kerosene and 1 part of Atmos 300 (emulsifier; trademark of Atlas Chemical Co.). The vessel is then equipped with a valve and 40 parts of propellant (liquefied petroleum gas) is charged through the valve into the aerosol vessel under pressure to give each of water-based aerosols.

Formulation Example 10

A solution prepared by dissolving 0.3 g of the present compound (A), (B) or (C) and 0.3 g of d-allethrin in 20 ml of acetone is homogeneously mixed with 99.4 g of a carrier for a mosquito-coil (mixture of Tabu powder, Pyrethrum marc and wood powder at the ratio of 4:3:3). After 120 ml of water is added, the mixture is kneaded sufficiently, molded and dried to give each of mosquito-coils.

Formulation Example 11

Ten milliliters (10 ml) of solution is prepared by dissolving 0.4 g of the present compound (A), (B) or (C) and 0.4 g of piperonyl butoxide in acetone. A half milliliter (0.5 ml) of the obtained solution is impregnated with a base material for mosquito-mat (a plate of compacted fibrils of a mixture of pulp and cotton linters: 2.5 cm×1.5 cm×0.3 cm) homogeneously to give each of mosquito-mats.

Formulation Example 12

A solution prepared by dissolving 10 mg of the present compound (A), (B) or (C) in 0.5 ml of acetone is mixed homogeneously with 5 g of solid feed powder for animals (solid feed powder for breeding : CE-2 manufactured by Japan Kurea Co., Ltd.). Then acetone is removed by air drying to obtain each of 0.5% poison baits.

Formulation Example 13

An acetone dilution containing the present compound (A), (B) or (C) is impregnated with non-woven cloth so that the concentration of the present compound is 1 g/1 $m^2$ and the acetone is air-dried to give each of acaricidal sheets.

The test examples below show that the present compounds are useful as an active ingredient for controlling harmful arthropods.

Test Example 1

Filter paper of 5.5 cm in diameter was laid in the bottom of a polyethylene cup (diameter: 5.5 cm). After 0.7 ml of a 500 ppm aqueous dilution obtained by diluting the formulation of the test compound prepared according to the formulation example 1 was dropped on the filter paper, 30 mg of sucrose was scattered. Two male German cockroaches (*Blattella germanica*) were left in the polyethylene cup with a cover. After six days, the mortality of the German cockroaches was examined. As a result, it was found that the present compound (A), (B) and (C) exhibited the mortality of 100%.

Test Example 2

Filter paper of 5.5 cm in diameter was laid in the bottom of a polyethylene cup (diameter: 5.5 cm). After 0.7 ml of a 500 ppm aqueous dilution obtained by diluting the formulation of the test compound prepared according to the formulation example 1 was dropped on the filter paper, 30 mg of sucrose was scattered. Ten female houseflies (*Musca domestics*) were left in the cup with a cover. After one day, the mortality of the houseflies was examined. As a result, it was found that the present compound (A), (B) and (C) exhibited the mortality of 100%.

Further, the following example shows that the present compound (A):

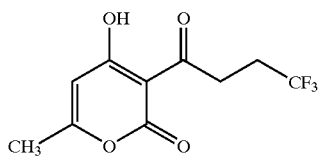

(A)

gives better effect than the reference compound:

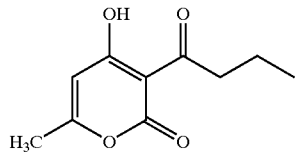

described in JP51-19126A as Compound No.2.

Test Example 3

A solution (30 g/l) for each of the present compound (A) and the reference compound was prepared by diluting with acetone. The acetone solution (0.5 µl) was applied to 10 female houseflies (*Musca domestics*) at the back thoracic region (active ingredient: about 15 µg/one housefly) by a microsyringe and the houseflies were left with water and feed in a plastic cup. After 24 hours, the mortality (%) was examined (three replicate). The results are given below.

|  | Mortality (%) |
| --- | --- |
| The present compound (A) | 100 |
| The Reference compound | 3.3 |

What is claimed is:

1. A pyrone compound given by formula (1)

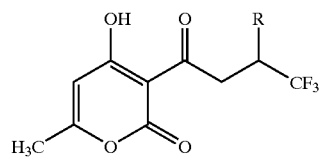

(1)

wherein R represents a trifluoromethyl group, hydrogen atom or methyl group.

2. A pyrone compound according to claim 1, wherein R represents trifluoromethyl group.

3. A pyrone compound according to claim 1, wherein R represents hydrogen atom.

4. A pyrone compound according to claim 1, wherein R represents methyl group.

5. A pesticidal composition comprising a pyrone compound given by formula (1)

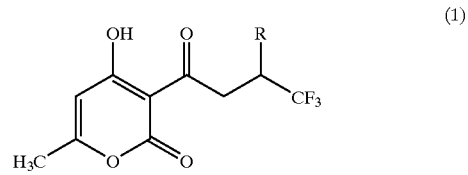

(1)

wherein R represents a trifluoromethyl group, hydrogen atom or methyl group, and a carrier.

6. A pesticidal composition according to claim 5, wherein R represents trifluoromethyl group.

7. A pesticidal composition according to claim 5, wherein R represents hydrogen atom.

8. A pesticidal composition according to claim 5, wherein R represents methyl group.

9. A method for controlling pests which comprises applying an effective amount of a pyrone compound given by formula (1)

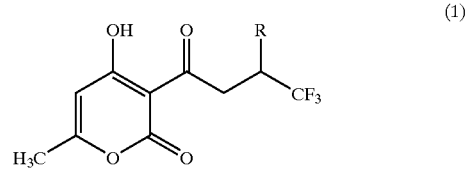

(1)

wherein R represents a trifluoromethyl group, hydrogen atom or methyl group, to pests or a place where pests inhabit.

* * * * *